United States Patent [19]

Hirano et al.

[11] Patent Number: 5,031,630
[45] Date of Patent: Jul. 16, 1991

[54] AUTOMATIC BLOOD PRESSURE MEASURING APPARATUS

[75] Inventors: Hitoshi Hirano, Gifu; Yoshimasa Kondo; Masahiro Uemura, both of Komaki, all of Japan

[73] Assignee: Colin Electronics Co., Ltd., Japan

[21] Appl. No.: 442,218

[22] Filed: Nov. 28, 1989

[30] Foreign Application Priority Data

May 6, 1989 [JP] Japan .................. 1-52508[U]

[51] Int. Cl.$^5$ .............................................. A61B 5/025
[52] U.S. Cl. ...................................... 128/680; 128/682
[58] Field of Search ............... 128/672, 677, 679, 680, 128/682, 686, 715; 606/204, 205, 206

[56] References Cited

U.S. PATENT DOCUMENTS

| 1,301,375 | 4/1987 | Medi | 128/680 |
| 2,087,238 | 2/1982 | Ichinomiya | 128/680 |
| 4,546,775 | 10/1985 | Medero | 128/680 |
| 4,790,325 | 12/1988 | Lee | 128/682 |
| 4,947,855 | 8/1990 | Yokoe et al. | 128/672 |

Primary Examiner—William E. Kamm
Assistant Examiner—Scott R. Akers
Attorney, Agent, or Firm—Oliff & Berridge

[57] ABSTRACT

An automatic blood pressure measuring apparatus, including an inflatable cuff having an elongate configuration, the inflatable cuff being wound around a body portion of a subject, for pressing an arterial vessel of the subject via a body surface over the arterial vessel, a detecting device for detecting at least one Korotkoff sound produced from the arterial vessel as the pressing force of the inflatable cuff applied to the arterial vessel is varied, and a determining device for determining at least one blood pressure value of the subject based on the detected at least one Korotkoff sound, the detecting device being located in a middle area, as viewed in a direction of width of the inflatable cuff, of an inner surface of the inflatable cuff which surface contacts the body portion of the subject.

14 Claims, 4 Drawing Sheets

AUTOMATIC BLOOD PRESSURE MEASURING APPARATUS

BACKGROUND OF THE INVENTION

1. Field of the Invention

The present invention generally relates to an automatic blood pressure measuring apparatus, and particularly to such an apparatus which measures blood pressure of a subject based on Korotkoff sounds produced from an arterial vessel of the subject.

2. Discussion of the Prior Art

There is known an automatic blood pressure measuring instrument which includes (a) an inflatable cuff having an elongate configuration, the inflatable cuff being wound around a body portion of a subject, for pressing an arterial vessel of the subject via a body surface over the arterial vessel, (b) a detector such as a microphone, for detecting at least one Korotkoff sound produced from the arterial vessel as the pressing force of the inflatable cuff applied to the arterial vessel is varied, and determining system for determining at least one blood pressure value of the subject based on the detected at least one Korotkoff sound.

In the above-indicated conventional instrument, the microphone or other Korotkoff sounds detector is positioned in a distal end area of the cuff which area is more remote from the heart of the subject than the other, proximal end area of the cuff. Accordingly, for example in the event that the subject is in a condition of shock and his or her pulsation is not strong enough, it has conventionally been experienced that the microphone cannot detect Korotkoff sounds with sufficiently great magnitudes, and therefore that accurate blood pressure measurement is difficult.

SUMMARY OF THE INVENTION

It is therefore an object of the present invention to provide an automatic blood pressure measuring apparatus which assures accurate and reliable blood pressure measurement even in the event that subject's pulsation is weak, or not strong.

The Inventor have conducted various researches and studies, and found that, as the position where the Korotkoff sounds detecting means is provided is moved from the distal end area of a cuff to the middle area thereof as viewed in a direction of width thereof, magnitude of the Korotkoff sounds detected is increased. The present invention has been developed based on this finding.

According to the principle of the present invention, there is provided an automatic blood pressure measuring apparatus with an inflatable cuff having an elongate configuration, the inflatable cuff being wound around a body portion of a subject, for pressing an arterial vessel of the subject via a body surface over the arterial vessel; a detector for detecting at least one Korotkoff sound produced from the arterial vessel as the pressing force of the inflatable cuff applied to the arterial vessel is varied, and a system for determining at least one blood pressure value of the subject based on the detected at least one Korotkoff sound, the apparatus being characterized in that the detector is located in a middle area, as viewed in a direction of width of the inflatable cuff, of an inner surface of the inflatable cuff which surface contacts the body portion of the subject.

In the automatic blood pressure measuring apparatus constructed as described above, the Korotkoff sounds detector is positioned in the middle area of the inner surface of the cuff as viewed in the direction of width of the cuff. For this reason, the detector detects Korotkoff sounds having sufficiently high magnitudes. Therefore, even in the event that subject's pulsation is weak, or not sufficiently strong, the present apparatus enables accurate and reliable blood pressure measurement to be carried out on the subject.

According to a feature of the present invention, the apparatus further includes a second detector for detecting at least one proximal arterial sound produced from the arterial vessel as the pressing force of the inflatable cuff applied to the arterial vessel is varied. The second detector employs a plurality of first sensing elements located in a proximal end area of the inner surface of the inflatable cuff and arranged in a direction of length of the inflatable cuff, each of the plurality of first sensing elements generating an electric signal representing the detected at least one proximal arterial sound.

According to another feature of the invention, the detector has a plurality of second sensing elements arranged in the direction of length of the inflatable cuff, each of the plurality of second sensing elements being aligned with a corresponding one of the plurality of first sensing elements in the direction of width of the inflatable cuff, and generating an electric signal representing the detected at least one Korotkoff sound.

According to yet another feature of the invention, the apparatus further includes a selector for selecting as an optimum first sensing element one of the plurality of first sensing elements such that the sound detected by the optimum first sensing element has a greatest magnitude of all the sounds detected by the plurality of first sensing elements, and selecting as an optimum second sensing element one of the plurality of second sensing elements such that the selected optimum second sensing element is aligned with the optimum first sensing element in the direction of width of the inflatable cuff.

According to a further feature of the invention, the apparatus further includes a collector for collecting, at least one Korotkoff sound, the collector collects, when the optimum first sensing element detects each of the at least one proximal arterial sound, a sound detected by the optimum second sensing element between a first and a second time point which are apart from each other and which are subsequent by respective first and second time lengths to the time of detection of the each of the at least one proximal arterial sound, as a Korotkoff sound corresponding to the each of the at least one proximal arterial sound. The determining system determines the at least one blood pressure value based on the thus collected at least one Korotkoff sound. The first and second time lengths may be 50 milliseconds and 350 milliseconds, respectively. In this case, the apparatus can accommodate some misalignment between the positions of the Korotkoff sounds detector and the underlying arterial vessel, and therefore even a person who is not skilled in handling cuffs, can carry out blood pressure measurement with satisfactory accuracy.

In a preferred embodiment of the present invention, the determining system determines as a maximum blood pressure of the subject a value of pressure in the inflatable cuff at the time of detection of a first Korotkoff sound as the pressure of the cuff is decreased from a predetermined pressure level sufficiently higher than an estimated maximum blood pressure of the subject, and determines as a minimum blood pressure of the subject a value of the cuff pressure at the time of detection of a last Korotkoff sound as the cuff pressure is decreased.

In another embodiment of the present invention, the apparatus further comprises display means for displaying the at least one blood pressure value determined by the determining means.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
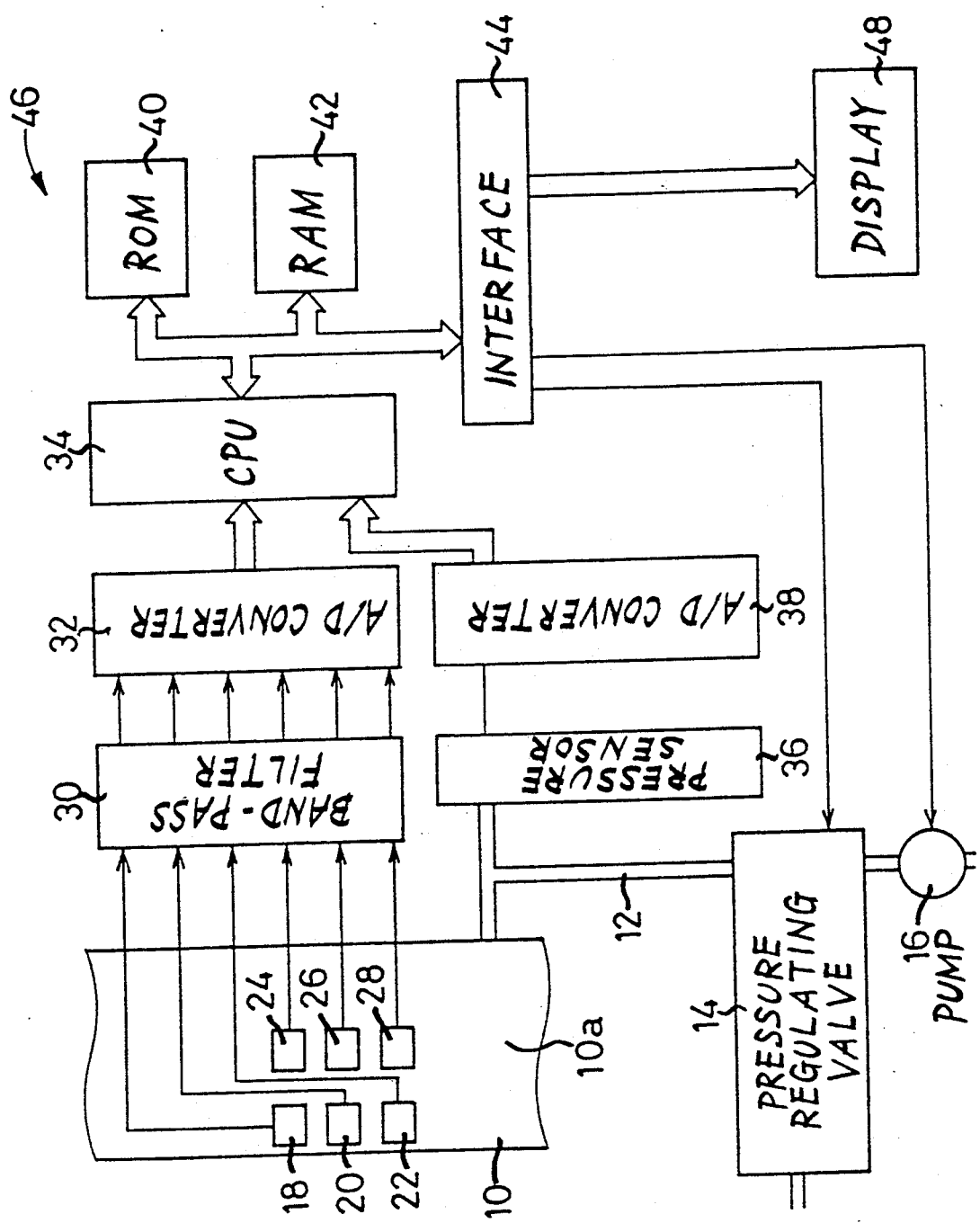
FIG. 1 is a block diagram for illustrating the construction of an automatic blood pressure measuring apparatus embodying the present invention.

Referring first to FIG. 1 there is shown the automatic blood pressure measuring apparatus of the present invention. In the figure reference numeral 10 designates an inflatable cuff having a band-like elongate configuration. The cuff 10 contains therein a rubber bag which is connected to a piping 12, and is wound around a body portion (e.g., upper arm) of a subject (e.g., patient) for pressing an artery via body surface over the artery. The piping 12 is connected to a pump 16 via a pressure regulating valve 14.

Responsive to a drive signal generated by a control device 46 (described below), the pressure regulating valve 14 checks deflation of the cuff 10 and simultaneously allows pressurized air to be supplied from the pump 16 to the cuff 10, for increasing air pressure in the rubber bag of the cuff 10. Meanwhile, when the cuff 10 is deflated slowly, namely, at a comparatively low rate, the valve 14 is operated to check the pressurized air supply from the pump 16 to the cuff 10 and simultaneously allows slow deflation of the pressurized air from the cuff 10 into ambient atmosphere.

On an inner surface 10a of the cuff 10 which surface is to contact the body surface of the subject, six piezoelectric sheets 18, 20, 22, 24, 26, 28 are provided. Each piezoelectric sheet generates an electric signal representing oscillations or strains applied thereto, based on piezoelectric effect. More specifically described, the first three sheets 18, 20, 22 are arranged in a proximal end area, as viewed in a direction of width of the cuff 10, of the inner surface 10a along a direction of length of the cuff 10 which direction intersects a direction of extension of the artery. The proximal end area of the cuff surface 10a is nearer to the heart of the subject than the other, distal end area thereof. The other, second three sheets 24, 26, 28 are arranged in a middle area, as viewed in the direction of width of the cuff 10, of the inner surface 10a along the direction of length of the cuff 10, such that each of the second sheets 24, 26, 28 is aligned with a corresponding one of the first three sheets 18, 20, 22 in the direction of width of the cuff 10. The first group of sheets 18–22 detect proximal arterial sounds transmitted from the artery to the proximal end area of the cuff 10. Meanwhile, the second group of sheets 24–28 detect Korotkoff sounds transmitted from the artery to the middle area of the cuff 10.

The signals generated by the piezoelectric sheets 18–28 are supplied to a first analog to digital (A/D) converter 32 via a band pass filter 30. The A/D converter 32 converts the received signals into corresponding digital signals, which are supplied to a central processing unit (CPU) 34. The band pass filter 30 possesses a "cut-off" frequency range, and allows passing therethrough of only signal components in a specific frequency range covering frequencies of the proximal arterial sounds and Korotkoff sounds which are produced from the artery in synchronization with heartbeat of the subject as the pressing force of the cuff 10 applied to the artery is varied.

The piping 12 is also connected to a pressure sensor 36 which generates an electric signal representing the air pressure in the cuff 10. The pressure signal generated by the pressure sensor 36 is supplied to a second analog to digital (A/D) converter 38, which converts the received signal to a corresponding digital signal and supplies the digital signal to the CPU 34.

The CPU 34 cooperates with a read only memory (ROM) 40, a random access memory (RAM) 42 and an interface circuit 44 to constitute the previously-mentioned control device ("microcomputer") 46. The CPU 34 processes the received signals according to software program pre-stored in the ROM 40 by utilizing a temporary storage function of the RAM 42, and generates drive signals to the pressure regulating valve 14 and the pump 16 via the interface circuit 44. In addition, the CPU 34 operates for determination of blood pressure of the subject, according to the blood pressure determination algorithm (described below) pre-stored in the ROM 40, and commands a display 48 to display the determined blood pressure.

Hereinafter there will be described the operation of the automatic blood pressure measuring apparatus constructed as described above, in connection with the flow charts of FIGS. 2 and 3.

Initially, the cuff 10 is wound around a body portion (e.g., upper arm) of a subject such that the six piezoelectric sheets (first and second sensing elements) 18, 20, 22, 24, 26, 28 are generally aligned, on the body surface, with an underlying artery. Then, upon operation of an activation switch (not shown) the control of the CPU 34 begins with step S1 (FIG. 2) in which the pump 16 is actuated and the pressure regulating valve 14 is operated to permit the pressurized air from the pump 16 to be supplied to the cuff 10, so that the air pressure in the cuff 10 is increased rapidly, namely, at a comparatively high rate. Step S1 is followed by step S2 in which it is judged whether or not the cuff pressure P (air pressure in the cuff 10) detected by the pressure sensor 36 has exceeded a target pressure level $P_m$, which is predetermined to be sufficiently higher than an estimated maximum blood pressure of the subject. At an early stage of the cuff inflation, the judgement in Step S2 is negative ("NO"), steps S1 and S2 are repeated. Meanwhile, if the judgement in step S2 turns to be affirmative ("YES"), namely, if it is judged in step S2 that the cuff pressure P has exceeded the target pressure level $P_m$, the control proceeds with step S3 in which the pump 16 is stopped and the pressure regulating valve 14 is operated to slowly deflate the cuff 10, so that the cuff pressure P is decreased at a comparatively low rate of 2 to 3 mmHg/sec, which rate is suitable for blood pressure measurement.

Following initiation of the slow deflation of the cuff 10 in step S3, step S4 is effected in which it is judged whether or not any one of the six piezoelectric sheets 18-28 has detected an arterial sound produced from the artery, based on the electric signals supplied from the sheets 18-28. If the judgement in step S4 is negative, step S4 is repeated and the control of the CPU 34 remains at step S4. On the other hand, if the judgement in step S4 is affirmative, the control proceeds to step S5 that is the Korotkoff sounds collection routine, which is effected according to the flow chart of FIG. 3.

In step SS1 (FIG. 3) the signal from each of the six piezoelectric sheets 18-28 is stored as sound data in the RAM 42. The sound data originating from each first sensing element 18, 20, 22 contain proximal arterial sounds, while the sound data originating from each second sensing element 24, 26, 28 contain Korotkoff sounds. Step SS1 is followed by step SS2 in which the magnitudes of the sounds detected by the three first sensing elements 18, 20, 22 are compared with each other, based on the corresponding sound data stored in the RAM 42, and in which an optimum first sensing element is selected such that the sound detected by the selected optimum first sensing element has the greatest magnitude of all the sounds detected by the three elements 18, 20, 22.

SS2 is followed by step SS3 in which an optimum second sensing element is selected from the three second sensing elements 24, 26, 28 such that the selected optimum second sensing element is aligned with the optimum first sensing element in the direction of width of the cuff 10. For example, in the event that the first sensing element 20 provides the greatest or maximum proximal arterial sound of the three first sensing elements 18, 20, 22 positioned in the proximal end area of the inner surface 10a of the cuff 10, the element 20 is selected as the optimum first sensing element, and the second sensing element 26 positioned in alignment with the element 20 is selected as the optimum second sensing element out of the three second sensing elements 24, 26, 28 positioned in the middle area of the cuff surface 10a.

Step SS3 is followed by step SS4 in which it is judged whether or not the optimum second sensing element has detected, following detection of a proximal arterial sound by the optimum first sheet, a sound within a time window defined by and between a first and a second time point which are apart from each other and which are subsequent by respective first and second time lengths to the time of detection of that proximal arterial sound by the optimum first sensing element. The sound, if detected, is collected as a Korotkoff sound corresponding to that proximal arterial sound detected by the optimum first sensing element. The above-indicated time window "opens" for a predetermined duration of time within which a proper Korotkoff sound is expected to occur, and thereby serves for cutting off noise detected therebefore and thereafter by the optimum second sensing element. For example, the time window begins 50 ms (milliseconds), and ends 350 ms, after the time of detection of each proximal arterial sound by the optimum first sensing element. In other words, the above-indicated first and second time lengths associated with the first and second time points are 50 ms and 350 ms, respectively. In the present embodiment, if the magnitude of a sound detected by any sheet 18-28 is below a predetermined level, such a sound is discarded and not regarded as a proximal arterial sound or a Korotkoff sound.

Figure 2:
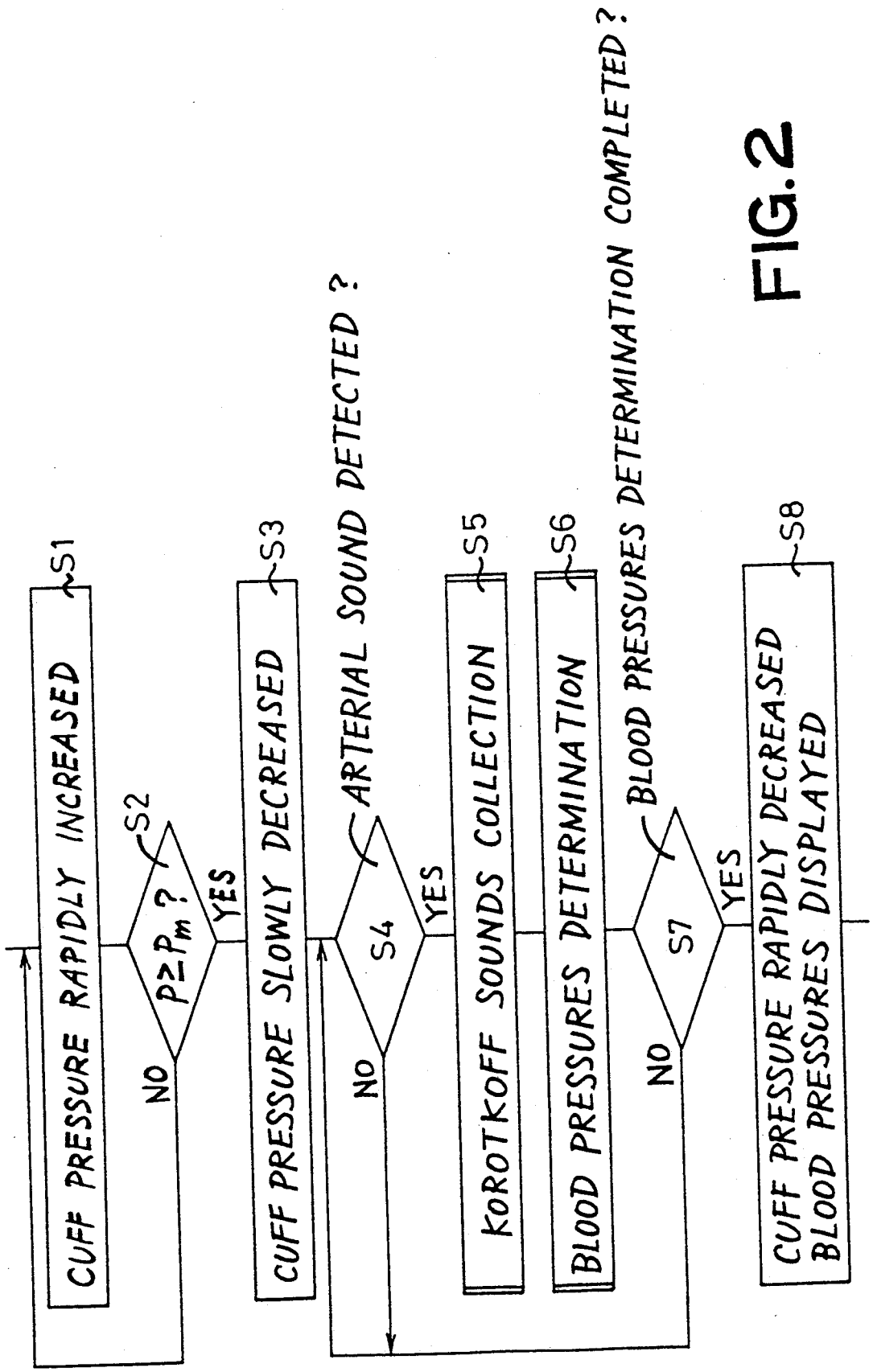
FIGS. 2 and 3 are flow charts according to which the apparatus of FIG. 1 is operated.
Figure 3:
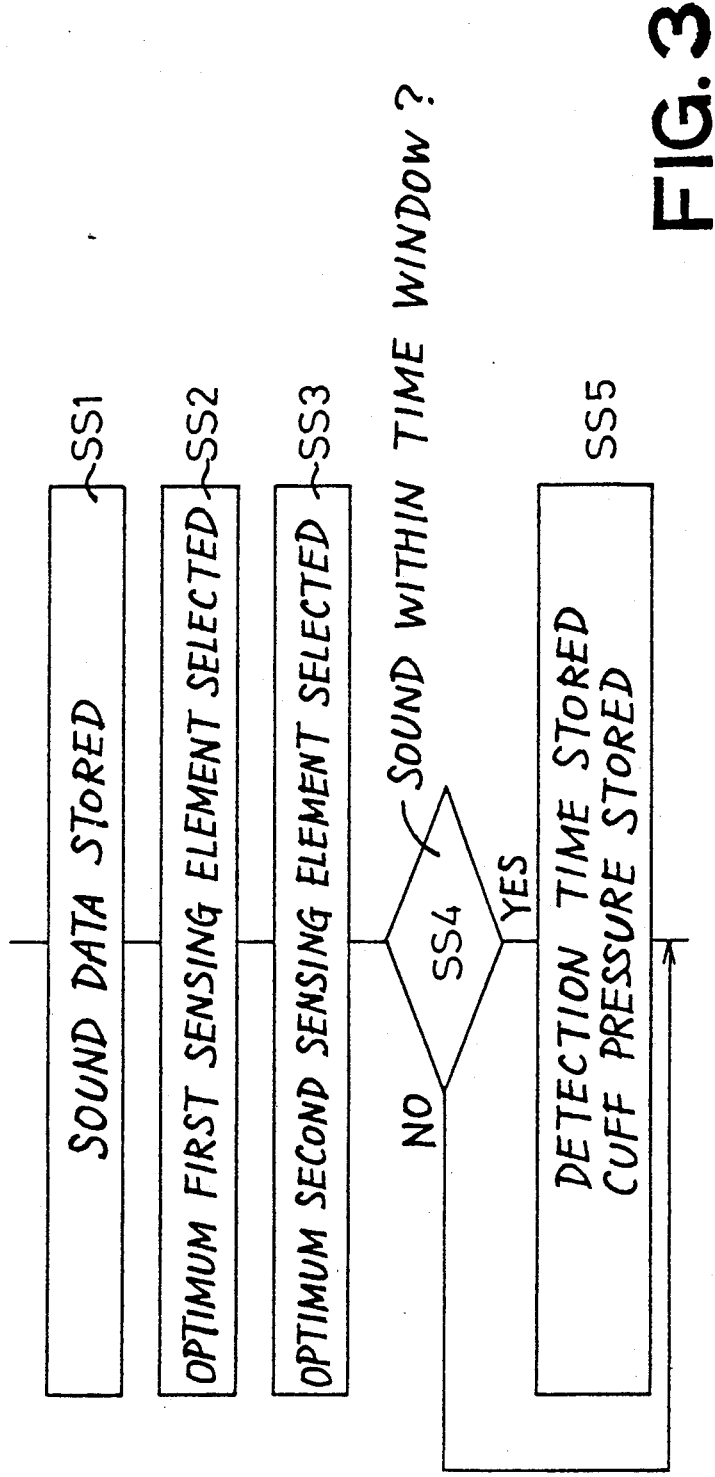

If the judgement in step SS4 is negative, the control quits the routine of FIG. 3, and proceeds with step S6 of FIG. 2. Meanwhile, if otherwise, namely, if it is judged in step SS4 that a Korotkoff sound has been detected, the control goes to step SS5 in which the time of detection of the Korotkoff sound and a value of the cuff pressure P at that detection time are stored in the RAM 42. In this event, too, the control quits the routine of FIG. 3, and proceeds with step S6 of FIG. 2. Thus, all the Korotkoff sounds produced from the artery as the cuff pressure P is slowly decreased, are collected with sufficient reliability.

Step S6 is the blood pressure determination routine in which a maximum and a minimum blood pressure of the subject are determined according to the blood pressure determination algorithm. In this routine, a value of cuff pressure P at the time of detection of a first one of the collected Korotkoff sounds is determined to be a maximum blood pressure of the subject, while a value of cuff pressure P at the time of detection of a last one of the collected Korotkoff sounds is determined to be a minimum blood pressure of the subject In other words, a cuff pressure value at the time of appearance of Korotkoff sounds is determined as a maximum blood pressure, while a cuff pressure value at the time of disappearance of Korotkoff sounds is determined as a minimum blood pressure.

Step S6 is followed by step S7 in which the blood pressure determination has been completed, namely, the maximum and minimum blood pressures of the subject have been determined in step S6. If it is judged that the maximum and/or minimum blood pressure have not been determined yet, for the reason, for example, that a last Korotkoff sound has not been determined yet, the control goes back to step S4, and the following steps. On the other hand, if it is judged in step S7 that the maximum and minimum blood pressures have been determined, that is, that the blood pressure measurement has been completed, the control goes to step S8 in which the cuff 10 is deflated rapidly, namely, at a comparatively high rate, so that the body portion such as the upper arm is released from the pressing under the cuff 10, and in which the thus determined maximum and minimum blood pressures are displayed on the display 48.

Figure 4:
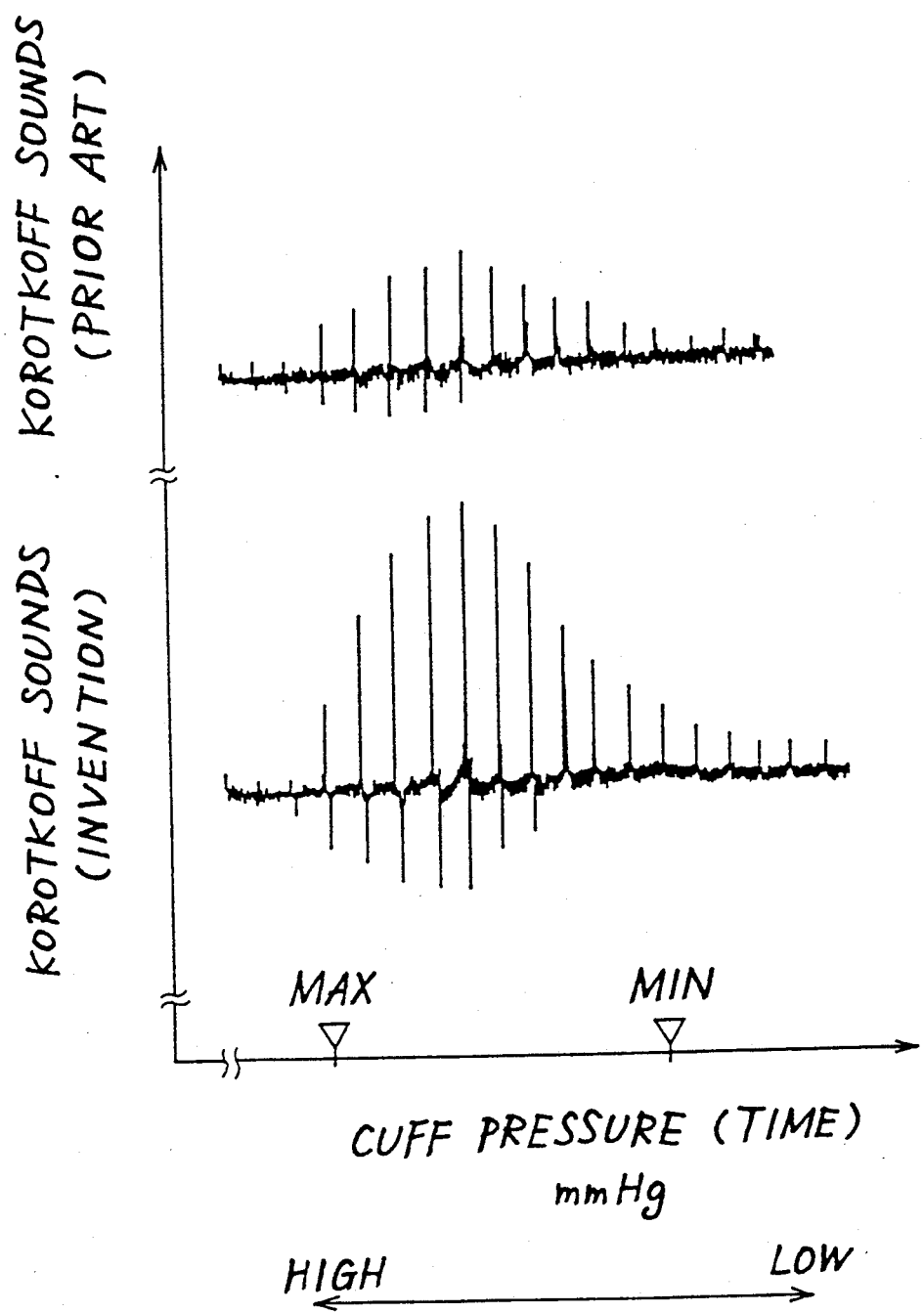
FIG. 4 is a graph representing the Korotkoff sounds detected by the apparatus of FIG. 1, compared with a graph of the Korotkoff sounds detected by the prior art apparatus.

As is apparent from the foregoing, in the present automatic blood pressure measuring apparatus, the Korotkoff sounds detecting sheets 24, 26, 28 are disposed in the middle area of the cuff 10 where the pressing force applied to the underlying artery via the body surface is sufficiently high and constant, and can accordingly detect Korotkoff sounds having sufficiently great magnitudes as shown in a lower part of the graph of FIG. 4. In contrast, in the conventional apparatus wherein the Korotkoff sounds detecting sensor is disposed in the distal end area of the cuff, the Korotkoff sounds detected by the sensor have low magnitudes as shown in an upper part of the graph of FIG. 4. Therefore, even in the event that pulsation of the artery of the subject is not strong enough, the present apparatus assures reliable and accurate blood pressure measurement.

With the cuff 10 inflated, the middle area of the cuff 10 is more proximate to the underlying artery than either end area of the cuff 10, and accordingly the Korotkoff sounds detecting sheets 24, 26, 28 positioned in that middle area are less adversely affected by misalignment between the sheets and the artery. For example, in the event that a microphone is positioned in an end area of a cuff, if the microphone is set on body surface in misalignment with an underlying artery, then the muscle and/or bone existing therebetween may more adversely attenuate magnitude of the Korotkoff sounds transmitted from the artery to the microphone, resulting in lowering magnitude of an electric signal representing the Korotkoff sounds which signal is generated by the microphone.

In the present embodiment, the three first sensing elements 18, 20, 22 each for detecting proximal arterial sounds (i.e., upstream-side arterial sounds) are arranged in the proximal end area of the inner surface 10a of the cuff 10 in the direction of length of the cuff 10, while the three second sensing elements 24, 26, 28 each for detecting Korotkoff sounds are arranged in the middle area of the cuff surface 10a in the same direction such that the second sensing elements are aligned with the corresponding first sensing elements in the direction of width of the cuff 10 which direction is generally parallel to the direction of extension of the underlying artery. And a pair of optimum first and second sensing elements (18, 24), (20, 26) or (22, 28) are selected. Therefore, even a person who is not skilled in handling cuffs can conduct, with this cuff 10, blood pressure measurement with sufficient reliability and accuracy.

In addition, in the present embodiment, when the optimum first sensing element 18, 20 or 22 detects each of proximal arterial sounds, a sound detected by the optimum second sensing element 24, 26 or 28 within a time window which is opened a first time duration after the time of detection of the each proximal arterial sound and is closed a second time duration after the same time, is collected as a Korotkoff sound corresponding to the each proximal arterial sound. The collected Korotkoff sounds are utilized for blood pressure determination. Thus, the present apparatus is free from the noise problem caused by physical activities of the subject and/or external forces applied to the cuff 10. For this reason, reliability and accuracy of blood pressure measurement are improved by using the present apparatus.

Furthermore, in the present apparatus, a first sensing element providing the maximum proximal arterial sound of all the three first sensing elements 18, 20, 22, is selected as the optimum first sensing element, while a second sensing element which is aligned with the optimum first sensing element is selected as the optimum second sheet from the three second sensing elements 24, 26, 28. Accordingly, even in the event that the cuff 10 is set at an upper arm of a subject, a pair of first and second elements out of the three pairs (18, 24), (20, 26) and (22, 28) are easily located in position directly above the underlying artery, namely, in accurate alignment with the underlying artery, and used as the optimum first and second elements for blood pressure measurement.

While the present invention has been described in its presently preferred embodiment, it is to be understood that the invention may be otherwise embodied.

For example, although in the illustrated embodiment the piezoelectric sheets 18-28 are used for detecting proximal arterial sounds and Korotkoff sounds, it is possible to employ microphones capable of detecting arterial sounds such as proximal arterial sounds and Korotkoff sounds.

In addition, while in the illustrated embodiment the three pairs of first and second sensing elements 18-28 are used for detecting proximal arterial sounds and Korotkoff sounds, it is possible to use a single pair of first and second sensing elements for detecting proximal arterial sounds and Korotkoff sounds, respectively, and furthermore it is possible to use a single second sensing element for detecting Korotkoff sounds, which element is disposed in the middle area of the inner surface of the cuff.

While the present invention has been described with detailed particularities of the presently preferred embodiment, it is to be understood that the invention may be embodied with various modifications, changes and improvements that may occur to those skilled in the art without departing from the spirit and scope of the invention as defined in the appended claims.

What is claimed is:

1. An automatic blood pressure measuring apparatus comprising;

an inflatable cuff having an elongate configuration, said inflatable cuff being adapted to be wound around a body portion of a subject, for pressing an arterial vessel of the subject via a body surface over said arterial vessel;

first detecting means for detecting at least one proximal arterial sound produced from said arterial vessel as the pressing force of said inflatable cuff applied to the arterial vessel is varied, said first detecting means being located in a proximal end area, as viewed in a direction of width of said inflatable cuff, of an inner surface of the inflatable cuff which surface contacts said body portion of the subject;

second detecting means for detecting at least one Korotkoff sound produced from said arterial vessel as the pressing force of said inflatable cuff applied to the arterial vessel is varied, said second detecting means being located in a middle area of said inner surface of the inflatable cuff as viewed in said direction of width of the inflatable cuff, said second detecting means being aligned with said first detecting means in the direction of width of the inflatable cuff;

collecting means for collecting at least one Korotkoff sound, said collecting means collecting, when said first detecting means detects each of said at least one proximal arterial sound, a sound detected by said second detecting means between a first and a second time point which are apart from each other and which are subsequent by respective first and second time lengths to the time of detection of said each of the at least one proximal arterial sound, as a Korotkoff sound corresponding to said each of the at least one proximal arterial sound; and determining means for determining at least one blood pressure value of the subject based on the collected at least one Korotkoff sound.

2. The apparatus as set forth in claim 1, wherein said first detecting means comprises a plurality of first sensing elements arranged in a direction of length of the inflatable cuff, each of said plurality of first sensing elements generating an electric signal representing the detected at least one proximal arterial sound.

3. The apparatus as set forth in claim 2, wherein said second detecting means comprises a plurality of second sensing elements arranged in the direction of length of said inflatable cuff, each of said plurality of second sensing elements being aligned with a corresponding one of said plurality of first sensing elements in the direction of width of the inflatable cuff, and generating an electric signal representing the collected at least one Korotkoff sound.

4. The apparatus as set forth in claim 3, further comprising selecting means for selecting as an optimum first sensing element one of said plurality of first sensing elements such that the sound detected by said optimum first sensing element has a greatest magnitude of all the sounds detected by the plurality of first sensing elements, and selecting as an optimum second sensing element one of said plurality of second sensing elements such that the selected optimum second sensing element is aligned with said optimum first sensing element.

5. The apparatus as set forth in claim 4, wherein said collecting means collects, when said optimum first sensing element detects each of said at least one optimum first sensing element detects each of said at least one proximal arterial sound, a sound detected by said optimum second sensing element between said first and second time points, as a Korotkoff sound corresponding to said each of the at least one proximal arterial sound.

6. The apparatus as set forth in claim 5, wherein said first and second time lengths are 50 milliseconds and 350 milliseconds, respectively.

7. The apparatus as set forth in claim 3, wherein each of said first and second sensing elements includes a piezoelectric sheet.

8. The apparatus as set forth in claim 1, wherein said determining means determines as a maximum blood pressure of the subject a value of pressure in said inflatable cuff at the time of detection of a first Korotkoff sound as the pressure of the cuff is decreased from a predetermined pressure level sufficiently higher than an estimated maximum blood pressure of the subject, and determines as a minimum blood pressure of the subject a value of the cuff pressure at the time of detection of a last Korotkoff sound as the cuff pressure is decreased.

9. The apparatus as set forth in claim 1, further comprising display means for displaying the at least one blood pressure value determined by said determining means.

10. An automatic blood pressure measuring apparatus comprising:
an inflatable cuff having an elongate configuration, said inflatable cuff being adapted to be wound around a body portion of a subject, for pressing an arterial vessel of the subject via a body surface over said arterial vessel;
first detecting means for detecting at least one proximal arterial sound produced from said arterial vessel as the pressing force of said inflatable cuff applied to the arterial vessel is varied, said first detecting means comprising a plurality of first sensing elements which are arranged in a proximal end area, as viewed in a direction of width of the inflatable cuff, of an inner surface of the inflatable cuff which surface contacts said body portion of the subject, along a direction of length of the inflatable cuff which direction intersects the arterial vessel;
second detecting means for detecting at least one Korotkoff sound produced from said arterial vessel, concurrently with the detection of the at least one proximal arterial sound by said first detecting means, said second detecting means comprising a plurality of second sensing elements which are arranged in a middle area, as viewed in the direction of width of the inflatable cuff, of said inner surface of said inflatable cuff along the direction of length of the inflatable cuff, such that each of said second sensing elements is aligned with a corresponding one of said plurality of first sensing elements in the direction of width of the inflatable cuff;
selecting means for selecting one of said plurality of first sensing elements such that the sound detected by the selected first sensing element has a greatest magnitude of all the sounds detected by the plurality of first sensing elements, and selecting one of said plurality of second sensing elements such that the selected second sensing element is aligned with said selected first sensing element in the direction of width of said inflatable cuff;
collecting means for collecting at least one Korotkoff sound, said collecting means collecting, when said selected first sensing element detects each of said at least one proximal arterial sound, a sound detected by said selected second sensing element between a first and a second time point which are apart from each other and which are subsequent by respective first and second time lengths to the time of detection of said each of the at least one proximal arterial sound, as a Korotkoff sound corresponding to said each of the at least one proximal arterial sound; and
determining means for determining at least one blood pressure value of the subject based on the thus collected at least one Korotkoff sound.

11. The apparatus as set forth in claim 10, wherein said first and second time lengths are 50 milliseconds and 350 milliseconds, respectively.

12. The apparatus as set forth in claim 10, wherein each of said first and second sensing elements includes a piezoelectric sheet.

13. The apparatus as set forth in claim 10, wherein said determining means determines as a maximum blood pressure of the subject a value of pressure in said inflatable cuff at the time of detection of a first Korotkoff sound as the pressure of the cuff is decreased from a predetermined pressure level sufficiently higher than an estimated maximum blood pressure of the subject, and determines as a minimum blood pressure of the subject a value of the cuff pressure at the time of detection of a last Korotkoff sound as the cuff pressure is decreased.

14. The apparatus as set forth in claim 10, further comprising display means for displaying the at least one blood pressure value determined by said determining means.

* * * * *